(12) United States Patent
Yuan et al.

(10) Patent No.: US 11,259,608 B2
(45) Date of Patent: Mar. 1, 2022

(54) ADAPTIVE FINGER SIZE RING

(71) Applicant: Hangzhou Megasens Technologies Co., Ltd., Zhejiang (CN)

(72) Inventors: Haiquan Yuan, Zhejiang (CN); Xiaobo Zeng, Zhejiang (CN)

(73) Assignee: Hangzhou Megasens Technologies Co., Ltd., Zhejiang (CN)

( * ) Notice: Subject to any disclaimer, the term of this patent is extended or adjusted under 35 U.S.C. 154(b) by 161 days.

(21) Appl. No.: 16/683,656

(22) Filed: Nov. 14, 2019

(65) Prior Publication Data

US 2020/0397101 A1     Dec. 24, 2020

(30) Foreign Application Priority Data

Jun. 18, 2019   (CN) .......................... 201920915581.X

(51) Int. Cl.
*A61B 5/1455*    (2006.01)
*A44C 9/02*      (2006.01)
*A61B 5/00*      (2006.01)

(52) U.S. Cl.
CPC ............ *A44C 9/02* (2013.01); *A61B 5/14552* (2013.01); *A61B 5/6826* (2013.01); *A61B 5/6838* (2013.01); *A61B 2562/0233* (2013.01)

(58) Field of Classification Search
CPC . A61B 5/1455; A61B 5/14552; A61B 5/6826; A61B 5/6838; A61B 2562/0233
See application file for complete search history.

(56) References Cited

U.S. PATENT DOCUMENTS

| | | | | |
|---|---|---|---|---|
| 4,789,123 A * | 12/1988 | Mattsson | ................. | A47B 1/04 108/80 |
| 6,654,621 B2 * | 11/2003 | Palatnik | ............. | A61B 5/14552 600/322 |
| 8,412,299 B2 * | 4/2013 | Kumazaki | ............ | A61B 5/6838 600/344 |
| 10,582,893 B2 * | 3/2020 | Lu | ....................... | A61B 5/14552 |
| 2010/0182126 A1 * | 7/2010 | Martis | .................. | A61B 5/6826 340/5.83 |

* cited by examiner

*Primary Examiner* — Eric F Winakur
(74) *Attorney, Agent, or Firm* — Elmore Patent Law Group, P.C.; Joseph Zucchero; Carolyn Elmore

(57) ABSTRACT

The present application discloses an adaptive finger size ring. The adaptive finger size ring in the present application includes: a first ring body, a second ring body, and two elastic devices. There is a clamping position between the first ring body and the second ring body, and the clamping position is used to clamp a finger. One end of the elastic device is connected to the first ring body, the other end is connected to the second ring body, and the two elastic devices are respectively located on two sides of the clamping position. The elastic device, the first ring body, and the second ring body form an annular shape. The elastic device is telescopic and has a tendency to shorten in length, so that the first ring body and the second ring body are in close contact with skin of the finger. Thus, a swelling feeling caused due to poor blood flow when the ring is worn for a long time can be avoided, and wearing comfort is improved.

7 Claims, 4 Drawing Sheets

ADAPTIVE FINGER SIZE RING

RELATED APPLICATION

This application claims priority to Chinese Application No. 201920915581.X, filed Jun. 18, 2019. The entire teachings of the above application are incorporated herein by reference.

TECHNICAL FIELD

The present application relates to blood oxygen saturation detection, and in particular, to an adaptive finger size ring.

BACKGROUND

Blood oxygen saturation is one of the key clinical physiological parameters. Currently, a monitor with a measurement host separated from a photoelectric sensor or a handheld blood oxygen saturation measurement instrument is mainly used for long term continuous measurement. The monitor is relatively large and is not suitable for wearing to perform continuous measurement. The handheld blood oxygen saturation measurement instrument is easy to wear but also easy to fall off. In order to solve the problem that the handheld blood oxygen saturation measurement instrument is easy to fall off, the degree of tightness of the existing handheld blood oxygen saturation measurement instrument are adjusted by using an elastic finger sleeve or a locking strap, but a problem of over-tightening is caused, and a radial pressure is exerted around a finger due to an axial (circumferential) force. Consequently, when the instrument is worn for a long time, poor blood flow and swelling feeling are easily caused, and wearing comfort is affected. In addition, because shapes of fingers are not the same, the photoelectric sensor is not in good contact with skin, and inaccurate measurement is caused.

SUMMARY

An objective of the present application is to provide an adaptive finger size ring, to implement the accuracy of blood oxygen saturation measurement and adaptability of different finger shapes and finger sizes under a comfortable wearing condition.

To solve the above technical problem, one aspect of the present application discloses an adaptive finger size ring, including a first ring body, a second ring body, and two elastic devices. There is a clamping position between the first ring body and the second ring body, and the clamping position is used to clamp a finger. One end of the elastic device is connected to the first ring body, the other end is connected to the second ring body, and the two elastic devices are respectively located on two sides of the clamping position. The elastic device, the first ring body, and the second ring body form an annular shape, the elastic device is telescopic, and has a tendency to shorten in length, so that the clamping position is reduced in size, the first ring body and the second ring body are in close contact with the finger to clamp the finger.

It can be understood that only the first ring body and the second ring body are in close contact with skin of the finger, and the elastic device is not in contact the skin of the finger, thus, the finger is partially under pressure, so that a swelling feeling caused due to poor blood flow when the ring is worn for a long time is avoided, wearing comfort is improved. In addition, the photoelectric detection device is in close contact with the finger, so that the accuracy of blood oxygen saturation measurement is ensured.

DETAILED DESCRIPTION OF THE EMBODIMENTS

Illustrative embodiments of the present application include, but are not limited to, an adaptive finger size ring.

Terms commonly used by persons skilled in the art are used in the present application to describe aspects of the illustrative embodiments, to convey essence of their work to other persons skilled in the art. However, it is apparent to the persons skilled in the art that some of the described aspects can be used to implement some alternative embodiments. For a purpose of explanation, specific numbers, materials, and configurations are described to provide a thorough understanding of the illustrative embodiments. However, it is apparent to the person skilled in the art that alternative embodiments can be implemented without specific details. In other instances, well-known features are omitted or simplified in order not to obscure the illustrative embodiments.

To make the objectives, technical solutions, and advantages of the present application clearer, the following further describes the embodiments of the present application in detail with reference to the accompanying drawings.

Figure 1:
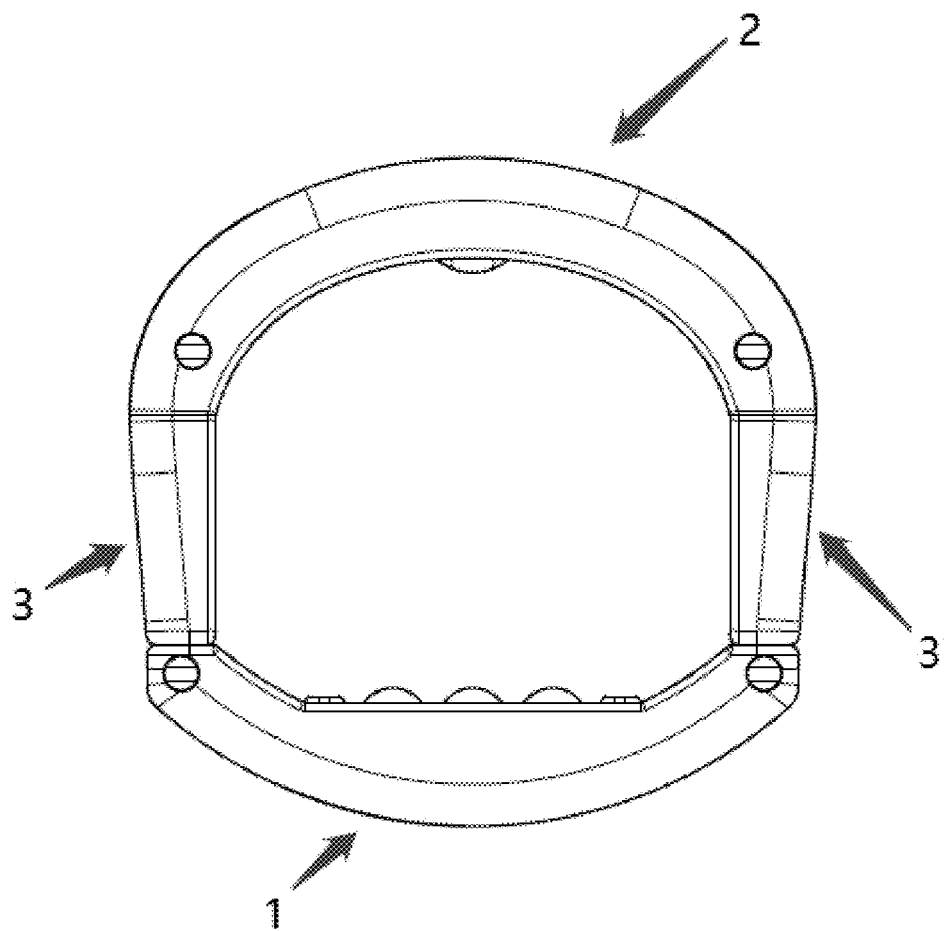
FIG. 1 is a schematic structural diagram of a ring in a closed state according to some embodiments of the present application.
Figure 2:
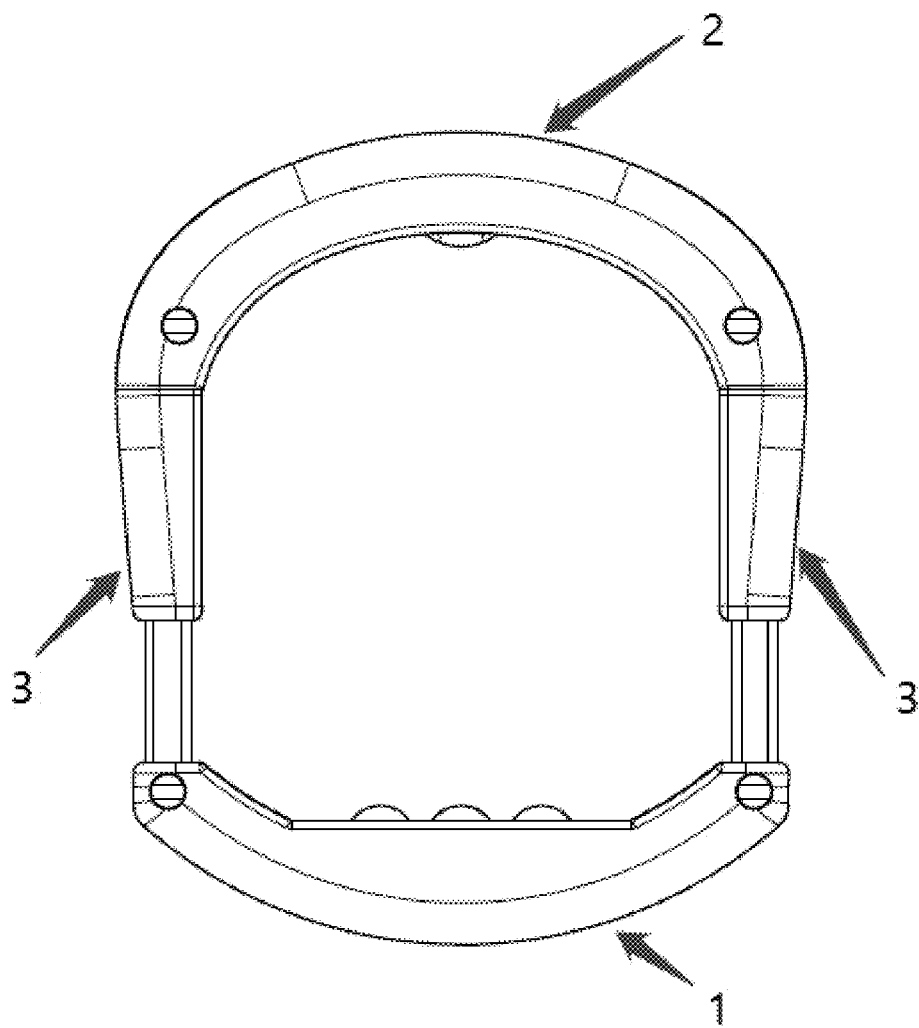
FIG. 2 is a schematic structural diagram of a ring in an opened state according to some embodiments of the present application.

According to some embodiments of the present application, an adaptive finger size ring is disclosed. FIG. 1 is a schematic structural diagram of the ring in a closed state, and the ring stays in the closed state when the ring is not under a force. FIG. 2 is a schematic structural diagram of the ring in an opened state. The first ring body 1 and the second ring body 2 of the ring are pulled apart, so that the first ring body 1 and the second ring body 2 are away from each other, and the ring becomes opened. In this case, the finger can be putted into or removed from the clamping position of the ring, to wear or remove the ring. When stop pulling apart the first ring body 1 and the second ring body 2 of the ring, the first ring body 1 and the second ring body 2 of the ring will be close to each other. In this case, if the finger is not putted into the clamping position of the ring, the ring will eventually return to the closed state. In this case, if the finger is putted into the clamping position of the ring, the first ring body and the second ring body are in close contact with skin of the finger, and the elastic device is not in contact with the finger, thus, the finger is partially under pressure, so that a swelling feeling caused due to poor blood flow when the ring is worn for a long time is avoided, wearing comfort is improved, and the ring can adapt to different shapes of fingers. In addition, the photoelectric detection device is in close contact with the finger, so that the accuracy of blood oxygen saturation measurement is ensured.

Specifically, referring to FIG. 1 and FIG. 2, the ring may include a first ring body 1, a second ring body 2, two elastic devices 3, a photoelectric detection device 5, and a power supply device 6. In addition, a clamping position is formed between the first ring body 1 and the second ring body 2.

The two elastic devices 3 are respectively located on two sides of the clamping position.

Figure 3:
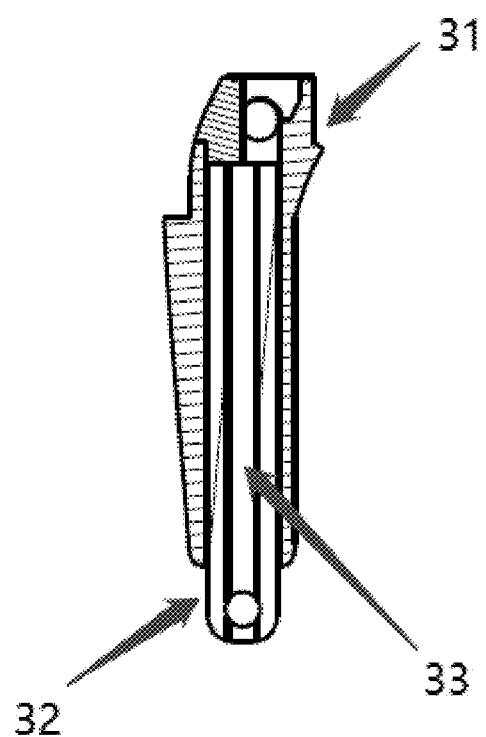
FIG. 3 is a schematic structural diagram of an elastic device of a ring according to some embodiments of the present application.

The elastic device 3, the first ring body 1, and the second ring body 2 form an annular shape. The elastic device 3 may be telescopic along the ring. As shown in FIG. 3, the elastic device 3 includes an outer casing 31, an inner casing 32, and an elastic member 33. The inner casing 32 is inserted into the outer casing 31, the elastic member 33 is located inside the outer casing 31, and the elastic member 33 connects the outer casing 31 and the inner casing 32. With a pull, the inner casing 32 is gradually pulled out from the outer casing 31, but after the pull disappears, the inner casing 32 is gradually pulled back into the outer casing 31 by the elastic member 33, so that the elastic member 33 has a tendency to shorten in length. In this embodiment of the present application, structures of the two elastic devices 3 are the same, but it can be understood that the structures of the two elastic devices 3 may be different, provided that lengths of the two elastic devices 3 can be adjusted, so that the clamping position can change in size, then it will also match the technical solution of the present application. At the same time, it can be understood that the elastic device 3 can have other functions or other names. This is not limited thereto.

In an embodiment of the present application, referring to FIG. 1 and FIG. 2, the outer casing 31 is fixedly connected to the second ring body 2, and the inner casing 32 is fixedly connected to the first ring body 1. It can be understood that, in another embodiment of the present application, the outer casing 31 is fixedly connected to the first ring body 1, and in this case, the inner casing 32 is fixedly connected to the second ring body 2. When the first ring body 1 and the second ring body 2 are pulled apart, and the first ring body 1 and the second ring body 2 are away from each other, the elastic member 33 is elongated, and the size of the clamping position becomes larger.

In this case, the finger can be putted into or removed from the clamping position to wear or remove the ring. When the finger is putted into the clamping position, stop pulling apart the first ring body 1 and the second ring body 2, the first ring body 1 and the second ring body 2 are pulled back to be close to each other by the elastic device 3, and the clamping position becomes smaller. Finally, the first ring body 1 and the second ring body 2 are in close contact with the skin of the finger, and the finger is closely clamped, and the finger is only partially compressed. Therefore, a swelling feeling caused due to poor blood flow can be avoided, and adaptability of different finger shapes and finger sizes is ensured under a premise of comfortable wearing, so that the smart bracelet is not easy to fall off and easy to wear.

Figure 4:
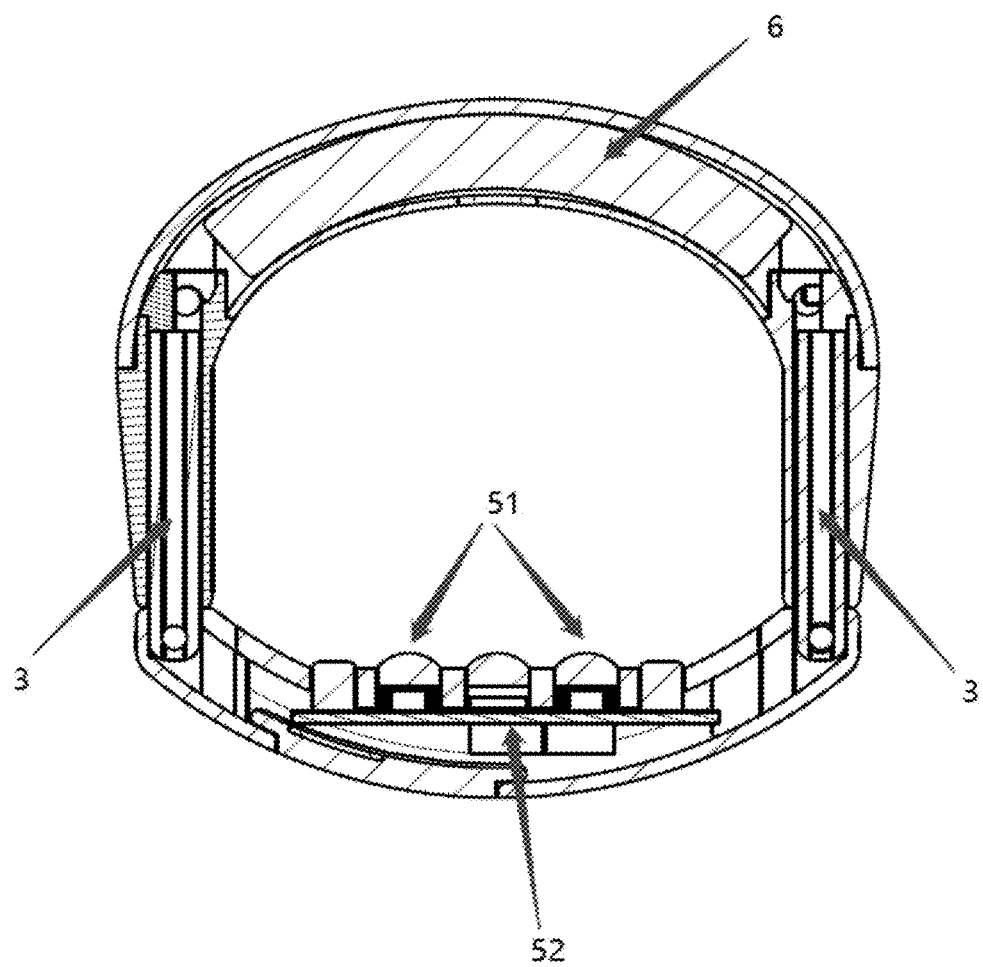
FIG. 4 is a cross-sectional view of a ring according to some embodiments of the present application.

In an embodiment of the present application, referring to FIG. 4, a photoelectric detection device 5 may include two light emitting diodes 51 and one photodiode 52. It can be understood that, the photoelectric detection device 5 may include one light emitting diode 51 or more than two light emitting diodes 51, and the photoelectric detection device 5 may include more than one photodiode 52. This is not limited herein. The first ring body 1 has a hollow structure, and may be made of a ceramic or metallic material, and the ceramic or metallic material has wear resistance and certain structural strength. The ring has a good texture and is decorative. The first ring body 1 can also be made of another material, and this is not limited herein. The photoelectric detection device 5 is disposed in the first ring body 1, and the light emitting diode 51 and the photodiode 52 protrude from one side of the first ring body that is close to the clamping position. When the ring is worn, the light emitting diode 51 and the photodiode 52 are in close contact with the skin of the finger so that accuracy of blood oxygen saturation measurement is ensured.

The second ring body 2 may have a hollow structure and may be made of a ceramic or metallic material. It can be understood that the second ring body 2 may be made of another material. The power supply device 6 is disposed in the second ring body 2, and is configured to supply power to the photoelectric measurement device 5. The power supply device 6 may be a battery or another device capable of supplying power. The power supply device 6 may have other functions or other names. This is not limited thereto. The power supply device 6 can be disposed elsewhere, such as within the first ring body 1. This is not limited herein.

The outer casing 31 and the inner casing 32 of the elastic device 3 may preferably be made of a metallic material or other materials may be used. The elastic member 33 may be a spring or a leaf spring or other elastic structures, or the elastic member may be made of an elastic material such as rubber. When a metal spring is selected as the elastic member 33, the elastic member 33 can also be used to connect the power supply device 6 and the photoelectric detection device 5 to form a circuit connection, so that the power supply device 6 can supply power to the photoelectric detection device.

In some embodiments of the present application, the first ring body 1, the second ring body 2, and the elastic device 3 are connected by screws or rivets or snaps, and functions of each unit are independent from each other, to implement modular design and production, so that efficiencies of research, development, and production is improved, and costs of research, development, and production are reduced.

A working procedure of the ring is as follows:

The light emitting diode 51 emits a red light with a wave length of 660 nm and a near-infrared light with a wave length of 940 nm to the finger as an incident source light, and a finger is used as a transparent container containing hemoglobin. The incident light transmits through the tissue bed of the finger and is reflected back by the bone. The photodiode 52 receives the reflected light and measures transmission intensity of the light transmitting through the tissue bed, to calculate hemoglobin concentration and blood oxygen saturation.

Further technical solutions of the present application are summarized in the following embodiments:

Embodiment 1 may include an adaptive finger size ring, including a first ring body, a second ring body, and two elastic devices. There is a clamping position between the first ring body and the second ring body, and the clamping position is used to clamp a finger. One end of the elastic device is connected to the first ring body, the other end is connected to the second ring body, and the two elastic devices are respectively located on two sides of the clamping position. The elastic device, the first ring body, and the second ring body form an annular shape. The elastic device is telescopic and has a tendency to shorten in length, so that the first ring body and the second ring body are in close contact with a finger.

Embodiment 2 may include the ring described in embodiment 1, and the elastic device includes an outer casing, an inner casing, and an elastic member. The outer casing is sleeved on an outer side of the inner casing. The elastic member connects the outer casing and the inner casing. The outer casing and the inner casing are respectively connected to the first ring body and the second ring body.

Embodiment 3 may include the ring described in embodiment 2, and further includes a photoelectric detection device. The photoelectric detection device is disposed on one side of the first ring body that is close to the clamping position.

Embodiment 4 may include the ring described in embodiment 3, and the photoelectric detection device includes a light emitting diode and a photodiode. The light emitting diode transmits an incident light which will be reflected by the finger later to the clamping position. The photodiode receives a reflected light reflected by the finger at the clamping position.

Embodiment 5 may include the ring described in embodiment 4, and further includes a power supply device. The power supply device is configured to supply power to the photoelectric detection device.

Embodiment 6 may include the ring described in embodiment 5, and the power supply device is disposed in the second ring body.

Embodiment 7 may include the ring described in embodiment 6, the elastic member is a spring, and the elastic member connects the power supply device and the photoelectric detection device, to implement a circuit connection between the power supply device and the photoelectric detection device.

Embodiment 8 may include the ring described in any one of embodiments 1-7. The first ring body and the second ring body have a hollow structure and are made of a ceramic or metallic material.

Embodiment 9 may include the ring described in any one of embodiments 1-7, and the inner casing and the outer casing are made of a metallic material.

Embodiment 10 may include the ring described in any one of embodiments 1-6, and the elastic member is a spring or a leaf spring or made of an elastic material.

In the accompanying drawings, some structural or method features may be shown in a particular arrangement and/or sequence. However, it should be understood that such a particular arrangement and/or ordering may not be required. Rather, in some embodiments, these features may be arranged in a manner and/or sequence different from that illustrated in the illustrative drawings. In addition, inclusion of structural or method features in a particular figure is not meant to imply that such features are required in all embodiments, and in some embodiments, these features may not be included or may be combined with other features.

It should be noted that in the examples and this specification of this patent, relational terms such as first and second are only used to distinguish one entity or operation from another, and do not necessarily require or imply that any actual relationship or sequence exists between these entities or operations. Moreover, the terms "include", "comprise", or any other variant is intended to cover a non-exclusive inclusion, so that a process, a method, an article, or a device that includes a list of elements not only includes those elements but also includes other elements which are not expressly listed, or further includes elements inherent to such process, method, article, or device. An element preceded by "includes a . . . " does not, without more constraints, preclude the existence of additional identical elements in the process, method, article, or device that includes the element.

Although the present application has been illustrated and described with reference to the preferred embodiments of the present invention, the person skilled in the art various should understand that changes in form and details can be made without departing from the spirit and scope of the application.

The invention claimed is:

1. An adaptive finger size ring, comprising a first ring body, a second ring body, and two elastic devices; wherein
   there is a clamping position between the first ring body and the second ring body, and the clamping position is used to clamp a finger;
   one end of each of the two elastic devices is connected to the first ring body, the other end is connected to the second ring body, and the two elastic devices are respectively located on two sides of the clamping position;
   the two elastic devices, the first ring body, and the second ring body form an annular shape; and
   each of the two elastic devices is telescopic and includes an elastic member that has a tendency to shorten in length, so that the first ring body and the second ring body are in close contact with the finger and the two elastic devices are not in contact with the finger when worn,
   the ring further comprising a photoelectric detection device and a power supply device,
   wherein each elastic member is a spring and connects the power supply device and the photoelectric detection device, to implement a circuit connection between the power supply device and the photoelectric detection device.

2. The ring according to claim 1, wherein each of the two elastic devices comprise an outer casing, an inner casing, and the elastic member;
   the outer casing is sleeved on an outer side of the inner casing;
   the elastic member connects the outer casing and the inner casing; and
   one of the outer casing and the inner casing is connected to the first ring body, and the other is connected to the second ring body.

3. The ring according to claim 2, wherein the photoelectric detection device is disposed on one side of the first ring body that is close to the clamping position.

4. The ring according to claim 3, wherein the photoelectric detection device comprises a light emitting diode and a photodiode;
   the light emitting diode transmits an incident light which will be reflected by the finger later to the clamping position; and
   the photodiode receives a reflected light reflected by the finger at the clamping position.

5. The ring according to claim 4, wherein the power supply device is disposed within the second ring body.

6. The ring according to claim 2, wherein the first ring body and the second ring body have a hollow structure, and are made of a ceramic or metallic material.

7. The ring according to claim 2, wherein the inner casing and the outer casing are made of a metallic material.

* * * * *